(12) United States Patent
Sato et al.

(10) Patent No.: US 8,591,925 B2
(45) Date of Patent: Nov. 26, 2013

(54) LIPOPHILICALLY SURFACE-TREATED POWDER HAVING EASY DISPERSABILITY AND COSMETIC BLENDED WITH SUCH A POWDER

(75) Inventors: Kazuo Sato, Saitama (JP); Hirofumi Ijiri, Yotsukaido (JP); Mitunari Saito, Saitama (JP); Masaharu Suzuki, Kasukabe (JP); Shinya Kuwazuru, Sumida-ku (JP)

(73) Assignee: Miyoshi Kasel, Inc., Saitama (JP)

( * ) Notice: Subject to any disclaimer, the term of this patent is extended or adjusted under 35 U.S.C. 154(b) by 177 days.

(21) Appl. No.: 13/262,893

(22) PCT Filed: Mar. 31, 2010

(86) PCT No.: PCT/JP2010/002400
§ 371 (c)(1),
(2), (4) Date: Oct. 4, 2011

(87) PCT Pub. No.: WO2010/116692
PCT Pub. Date: Oct. 14, 2010

(65) Prior Publication Data
US 2012/0027709 A1  Feb. 2, 2012

(30) Foreign Application Priority Data
Apr. 7, 2009  (JP) ................. 2009-092709

(51) Int. Cl.
*A61K 9/14* (2006.01)
*A61K 8/18* (2006.01)
*A61Q 1/12* (2006.01)

(52) U.S. Cl.
USPC ............. 424/401; 424/69; 424/489; 424/490; 424/497; 424/498

(58) Field of Classification Search
None
See application file for complete search history.

(56) References Cited

U.S. PATENT DOCUMENTS

| 6,482,441 B1 | 11/2002 | Hasegawa et al. |
| 2004/0175386 A1 | 9/2004 | Yoshikawa et al. |

FOREIGN PATENT DOCUMENTS

| JP | B2-6-59397 | 8/1994 |
| JP | A-7-196946 | 8/1995 |
| JP | A-8-104606 | 4/1996 |
| JP | A-9-268271 | 10/1997 |
| JP | B2-3079395 | 6/2000 |
| JP | A-2001-72527 | 3/2001 |
| JP | A-2001-181136 | 7/2001 |
| JP | A-2002-80748 | 3/2002 |
| JP | A-2005-82796 | 3/2005 |
| JP | A-2006-290878 | 10/2006 |
| JP | A-2007-291302 | 11/2007 |
| JP | A-2009-138121 | 6/2009 |
| JP | A-2009-179606 | 8/2009 |
| WO | WO 03/002076 A1 | 1/2003 |

OTHER PUBLICATIONS

Crocket; [online] retrieved from; http://www.uhv.edu/ac/newsletters/writing/grammartip2006.08.29.htm on Jan. 31, 2013; 2 pages.*
Kind; [online] retrieved from: http://dictionary.cambridge.org/dictionary/british/kind_2 on May 22, 2013; 2 pages.*
(Hart; A Manual of composition and rhetoric, 1871, p. 50).*
Parenthesis; Merriam Webster Dictionary [online] retrieved on Jan. 31, 2013 from: http://www.merriam-webster.com/dictionary/parenthesis; 4 pages.*
International Search Report issued in International Patent Application No. PCT/JP2010/002400 dated Jun. 22, 2010 (with translation).
International Preliminary Report on Patentability issued in International Application No. PCT/JP2010/002400 dated Nov. 15, 2011 (with translation).

* cited by examiner

*Primary Examiner* — Ernst Arnold
(74) *Attorney, Agent, or Firm* — Oliff & Berridge, PLC.

(57) ABSTRACT

Provided is a surface-treated powder, in which a powder is treated with a surface-treating agent composed of a mixture A+B including A: an alkyl alkoxy silane of a general formula (1): $(C_nH_{2n+1})_aSi(OC_mH_{2m+1})_b$ and B: one kind of a compound or two or more kinds of compounds selected from a reactive organo silicone of the following general formula (2): $(R^1{}_3SiO)(R^1{}_2SiO)_p(SiR^2{}_3)$ and a C12 to C22 saturated or unsaturated branched fatty acid. In the general formula (1), n is an integer of 1 to 18, m is an integer of 1 to 3, a, b represent an integer of 1 to 3, and a+b=4. In the general formula (2), $R^1$'s mutually independently represents a lower alkyl group having 1 to 4 carbon atoms or a hydrogen atom or a hydrogen atom, respectively, $R^2$ is any of an amino group, a hydrogen atom, a hydroxyl group and a C1-C4 lower alkoxy group, and p is an integer of 1 to 300.

9 Claims, No Drawings

LIPOPHILICALLY SURFACE-TREATED POWDER HAVING EASY DISPERSABILITY AND COSMETIC BLENDED WITH SUCH A POWDER

TECHNICAL FIELD

The present invention relates to a lipophilically surface-treated powder exhibiting easy dispersibility, and improved feeling in finished cosmetics, improved makeup effects and stability improved by using the surface-treated powder.

BACKGROUND TECHNIQUE

In the powder to be mixed into the cosmetics, the primary particle size ranges from nano order to around a few to several hundred microns, and the powder exists in the form of aggregate of particles of primary particles. The primary particle sizes of the powders are determined by the chemical composition and a range of the particulate sizes of that powder under consideration of a function to be exhibited in the cosmetics. For example, in the case of titanium dioxide, in order to improve the usability and protection from infrared rays, the primary particle sizes are set to particle sizes of several micrometers in a geometrically optical range; in order to exhibit a shielding power and a coloring power, they are set to particle sizes of near half wavelengths of visible light rays, that is, Mie scattering range; and in order to exhibit an ultraviolet ray shielding power, they are set to particle sizes of a Rayleigh scattering range considerably smaller than the wavelengths of the visible light rays.

As the powder particles are more dispersed in a state nearer to the set primary particle sizes, the functions possessed by the powder, that is, for example, characteristics sought for the cosmetics, such as the shielding effect, the coloring effect, an ultraviolet ray scattering effect, transparency, optical characteristics, skin adhesion, touch to skin and the like, can be exhibited to the utmost extent. However, the smaller the primary particle sizes of the powder are, the greater is the specific surface area, so that since the particles have increased contact points therebetween, the particles are more likely to be aggregated and consequently the dispersability is deteriorated. A number of surface-treating techniques have been proposed as certain measures to avoid this aggregation as much as possible, and prevent re-aggregation even with the lapse of time.

There are proposed a variety of surface-treating methods, for example, (1) a method in which a silicone oil (for instance, methyl polysiloxane, methyl hydrogen polysiloxane or alkyl silane with the number of carbon atoms of an alkyl portion being not more than 10) is dissolved into a solvent as a surface-treating agent, which is added and mixed into a powder, and the surface treatment is baked onto the powder by heating after the drying process; (2) a method in which, while a powder and octyl triethoxy silane or the like are being dispersed into an organic solvent by using a media grinder, the surface of the powder is treated with an organic silicon compound such as octyl triethoxy silane (Patent Document 1); (3) a method in which N-octyl trimethoxy silane or N-octyl triethoxy silane as an alkyl silane compound is stirred and mixed by a Henschel mixer, and a reaction is completed under heating, and the resultant is pulverized by a hammer mill (Patent Document 2); (4) a method in which a silicone compound such as methyl hydrogen polysiloxane or the like is emulsified by dispersing it in water, and surfaces of powder particles are coated by mixing the emulsion to the powder (Patent Document 3); (5) a jet method in which after a metal soap, an organic silicon compound in which a reactive group such as a hydrogen group or the like is bonded to a silicon atom, and a powder are mixed, the mixture is pulverized by a miller using an ejecting stream simultaneously with the surface treatment (Patent Document 4); and (6) a method in which in order to improve dispersability of a powder, coating is effected with surface treating agents for an A layer and a layer B by a jet method (Patent Document 5).

PRIOR ART DOCUMENT

Patent Documents

Patent Document 1: JP-A 08-104606
Patent Document 2: JP-A 2001-181136
Patent Document 3: JP-A 09-268271
Patent Document 4: JP-B 06-59397
Patent Document 5: JP-A 2002-80748

However, the dispersed state, in other words, the aggregated state of the powder differs depending upon the type, the treating amount, and the combination of the lipophilically surface treating agent. The surface-treating agent has a functional group, and when the powder is treated with a compound which causes polycondensation on reacting a base material of the powder or a compound solidifying at ordinary temperature, an aggregate or an agglomerate of the powder particles are induced. For example, methyl hydrogen polysiloxane, which has been conventionally used as a surface-treating agent for the cosmetic powders, is resinified through hydrolysis under the presence of OH groups and water at the surface of the inorganic powder particles, so that the surfaces of the particles are coated therewith. At that time, there is a problem that the aggregation occurs, so that easy dispersability cannot be obtained (Patent Documents 1 and 3).

Although some of surface treating agents such as alkyl silane, acryl silicone and the like have the dispersing power for the powder particles (pigment dispersability) as the compounds themselves, treatment with the alkyl alkoxy silane or the like alone causes less aggregation with the surface treating agent, but the ease of dispersibility needs to be further enhanced. On the other hand, there was a problem that sufficient dispersability could not be obtained in a liquid (Patent Document 2). Furthermore, in the case of the fatty acid-treated powder, straight-chain fatty acids having 14 or more carbon atoms are generally used. Although these compounds are solid at ordinary temperatures, it has a melting point of around 60° C. As to these surface treating agents, it is usual that a powder is treated by melting such a surface-treating agent at a temperature of not less than the melting point, or alternatively it is saponified and dissolved into an aqueous slurry containing a powder and the surface treatment is carried out through the formation of a polyvalent metal salt. The treatment with the solid material at ordinary temperatures is likely to cause aggregation and the dispersability is not good (Patent Document 4 and Patent Document 5).

SUMMARY OF THE INVENTION

Problems to be Solved by the Invention

The present invention is aimed at providing a lipophilically surface-treated powder, which can be easily dispersed even with weak mixing and stirring force with a Henschel mixer, a propeller mixer, a disperser mixer or the like, even in a powder-mixing system or a liquid-mixing system. In addition, the present invention is aimed at providing a cosmetic into which such a surface-treated powder is mixed and which is excellent in usability, cosmetic effects and cosmetic stability.

Measures to Solve the Problems

The present invention is directed to a surface-treated powder, in which a powder is treated with a surface-treating agent composed of a mixture (A+B) between (A) an alkyl alkoxy silane expressed by the following general formula (1) and (B) one kind of a compound or two kinds of compounds selected from a reactive organo silicone expressed by the following general formula (2) and a saturated or unsaturated branched fatty acid having 12 to 22 carbon atoms (including a salt form).

(Chemical Formula 1)

$$(C_nH_{2n+1})_aSi(OC_mH_{2m+1})_b \quad (1)$$

(In the formula, n denotes an integer of 1 to 18, m denotes an integer of 1 to 3, a, b denote an integer of 1 to 3, and a+b=4.)

(Chemical formula 2)

$$(R^1_3SiO)(R^1_2SiO)_p(SiR^2_3) \quad (2)$$

(In the formula, $R^1$s, which are all mutually independent, denote a lower alkyl group having 1 to 4 carbon atoms or a hydrogen atom, respectively, $R^2$ denotes any of an amino group, a hydrogen atom, a hydroxyl group and a lower alkoxy group having 1 to 4 carbon atoms, and p is an integer of 1 to 300.)

In the above, the wording "a surface-treating agent composed of a mixture (A+B) - - - " includes not only "a surface-treating agent composed of only a mixture (A+B) - - - " but also "a surface-treating agent composed of a mixture (A+B+C and the like) containing C and the like other than (A+B) and not losing the effects of the present invention".

In the following, preferred embodiments of the present invention are recited, and their arbitrary combinations are also preferred embodiments of the present invention, so long as particularly no contradiction occurs.
(1) The surface-treating agent is composed of the above alkyl alkoxy silane and the above reactive organo silicone.
(2) The surface-treating agent is composed of the alkyl alkoxy silane and the above branched fatty acid.
(3) In the general formula (1), n is 1 to 8.
(4) In the general formula (2), p is 2 to 50.
(5) The mixing ratio (weight) of the above (A):(B) is 1.0 to 29.0 parts:29.0 to 1.0 parts.
(6) The mixing ratio between the powder to be surface-treated and the surface-treating agent is that the surface-treating agent is 1 to 30 parts by weight per 100 parts by weight of the powder.
(7) The surface-treated powder is a surface-treated powder further pulverized by a jet mill.
(8) The surface-treated powder is a surface-treated powder usable for cosmetics.

The present invention is further directed to a cosmetic into which any of the surface-treated powders set forth in the above.

Effects of the Invention

The surface-treated powder according to the present invention is obtained in a state nearer to the primary particle sizes by surface-treating a powder to be surface-treated, such that the powder is surface-coated with the surface-treating agent in which, (A) the alkyl alkoxy silane expressed by the following general formula (1) and (B) one kind or two or more kinds of the above-specified compounds are combined. Since the obtained surface-treated powder exhibits easy dispersability, it can be easily dispersed in any form of powder-mixing systems and liquid-mixing systems. As a result, the surface-treated powder is excellent for example in terms of shielding power, a coloring power, an ultraviolet ray scattering effect, transparency, optical characteristics, adhesion to skin, touch, etc. In addition, the cosmetics into which the above powder is mixed provides improved makeup effects, and stability.

EMBODIMENTS TO CARRY OUT THE INVENTION

In the following, the present invention will be explained in detail, but the invention is not limited thereto.
(1) Powder The powder to be used in the present invention may be any of an inorganic powder and an organic powder, and the inorganic powder is preferably used. The surface-treated powder according to the present invention is suitable particularly as a surface-treated powder for cosmetic uses, but the powder is not particularly limited, so long as it can be usually used as a powder to be used in the cosmetics. For example, the powder can be boron nitride, sericite, natural mica, incinerated mica, synthetic mica, synthetic sericite, alumina, mica, talc, kaolin, bentonite, smectite, calcium carbonate, magnesium carbonate, calcium phosphate, silicic anhydride, magnesium oxide, tin oxide, iron oxide, yttrium oxide, chromium oxide, titanium dioxide, zinc oxide, cerium oxide, aluminum oxide, magnesium oxide, chromium hydroxide, iron blue, ultramarine blue, calcium phosphate, aluminum hydroxide, barium sulfate, magnesium sulfate, silicic acid, aluminum magnesium silicate, calcium silicate, barium silicate, magnesium silicate, aluminum silicate, strontium silicate, silicon carbide, magnesium fluoride, tungstic acid metal salts, magnesium aluminate, magnesium methasilicate aluminate, chlorohydroxy aluminum, clay, zeolite, hydroxyapatite, ceramic powder, spinel, mullite, cordierite, aluminum nitride, titanium nitride, silicon nitride, lanthanum, samarium, tantalum, terbium, europium, neodymium, Mn—Zn ferrite, Ni—Zn ferrite, silicon carbide, cobalt titanate, barium titanate, iron titanate, lithium cobalt titanate, cobalt aluminate, antimony-containing tin oxide, tin-containing indium oxide, magnetite, aluminum powder, gold powder, silver powder, platinum powder, copper powder, precious metal colloid, iron powder, zinc powder, cobalt blue, cobalt violet, cobalt green, low level titanium oxide, finely particulate titanium oxide, butterfly-shaped barium sulfate, flower petal-shaped zinc oxide, tetrapod-shaped zinc oxide, and finely particulate zinc oxide. As pearl pigments, pearl pigments such as titanium dioxide-coated mica, titanium dioxide-coated mica, titanium dioxide-coated synthetic mica, titanium dioxide-coated silica, titanium dioxide-coated synthetic mica, titanium dioxide-coated talc, zinc oxide-coated silica, titanium dioxide-coated colored mica, red iron oxide coated titanium mica, red iron oxide/black iron oxide-coated titanium mica, carmine-coated titanium mica, iron blue-coated titanium mica, and so on are recited. These powders can be used singly or in a state in which multiple powders are mixed or made into composite pigments.
(2) Surface-Treating Agent The surface-treating agent to be used in the present invention is composed of a mixture (A+B), which comprises (A) an alkyl alkoxy silane expressed by the following general formula (1) and (B) one kind of a compound or two or more kinds of compounds selected from a reactive organo silicone expressed by the following general formula (2) and a saturated or unsaturated branched fatty acid having 12 to 22 carbon atoms (including a salt form), and is used for surface-treating a powder.

(Chemical formula 3)

$$(C_nH_{2n+1})_a Si(OC_mH_{2m+1})_b \quad (1)$$

(In the formula, n denotes an integer of 1 to 18, m denotes an integer of 1 to 3, a, b denote an integer of 1 to 3, and a+b=4.)

(Chemical formula 4)

$$(R^1{}_3SiO)(R^1{}_2SiO)_p(SiR^2{}_3) \quad (2)$$

(In the formula, $R^1$s, which are mutually all independent, denote a lower alkyl group having 1 to 4 carbon atoms or a hydrogen atom, respectively, $R^2$ denotes any of an amino group, a hydrogen atom, a hydroxyl group and an alkoxy group having 1 to 4 carbon atoms, and p is an integer of 1 to 300.)

It is considered that the above alkyl alkoxy silane has a function to provide the surface-treated powder with an excellent pigment dispersion power, the above reactive organo silicone has a function to provide the powder with excellent easy dispersability through composite treatment with the alkyl alkoxy silane, and the above saturated or unsaturated branched fatty acid has a function to improve adhesion to an organic material such as to the skin, etc.

From the standpoint to provide the surface-treated powder with excellent pigment dispersion power, the number of n in the formula (1) of the alkyl alkoxy silane to be used in the present invention is preferably 1 to 8. For example, methyl triethoxy silane, hexyl triethoxy silane and octyl triethoxy silane are recited. It is a tendency that the greater the number of n, the lesser the pigment dispersability. From the standpoint to ensure the reactivity with the surface of the powder, the number of m in the formula (1) is limited to 1 to 3.

From the standpoint to provide the powder with more excellent easy dispersability through the composite treatment with the alkyl alkoxy silane, the above reactive organo silicone to be used in the present invention is preferably one having a trialkoxy group at one terminal in which p is 2 to 50. For example, compounds described in Japanese Patent No. 3079395 and JP-A 07-196946 are recited.

As the branched-chain saturated or unsaturated fatty acids having 12 to 22 carbon atoms, isotridecanoic acid, isomyristic acid, isopalmitic acid, isostearic acid, behenic acid and the like (including a salt form) are recited, for example. In the present invention, the above "saturated or unsaturated branched fatty acid having 12 to 22 carbon atoms" includes metal salts of Ca, Mg, Zn, Zr, Al, Ti and the like of the branched fatty acid. Particularly, isomyristic acid, isopalmitic acid and isostearic acid as the saturated branched fatty acids are preferable. The reason why the number of carbon atoms is limited to 12 or more is from the standpoint of aggregation prevention and reduction in irritating properties to the skin. The reason why number of carbon atoms is limited to 22 or less is from the standpoint of the adhesion to the pigment.

(3) Surface-Treating Method

As a method for surface-treating the powder with the surface-treating agent which is composed of the mixture comprising the alkyl alkoxy silane and one kind of a compound or two or more kinds of compounds selected from the surface-treating agents of the reactive organo polysiloxane and the saturated or unsaturated branched fatty acid having 12 to 22 carbon atoms, a publicly known method has only to be used. The powder is surface-treated by mixing and contacting the surface-treating agent to be used in the present invention with the powder for a given amount of time. As a preferable producing method, a method in which the powder is passed through a jet mill after the surface treatment. As the method in which the powder is passed through the jet mill after the surface treatment, the following two methods are recited, for example: (1) a method in which the powder is heated and dried by passing it through the jet mill after the surface-treating agent and the powder are mixed and dispersed in a drying manner or a wet manner and (2) a method in which the powder is passed through the jet mill after the surface-treating agent and the powder are mixed and dispersed in the dry manner or the wet manner, and heated and dried. In the case of coating the powder in which the sizes of the primary particles are not less than submicrons, a pulverizer such as a pin mill, a hammer mill or the like can be used instead of the jet mill.

As a mixing dispersion device to be used for mixing and contacting the above powder, a Henschel mixer, a ribbon blender, a Q mill, a kneader, a planetary mixer, a pony mixer, a Bumbary mixers, a ball mill, a dry-type sand mill, a wet-type sand mill, an attritor, disperser mixer, a homo mixer, an extruder and the like are recited. Further, these treatments may be carried out, while an energy such as a mechanochemical mechanical force, ultrasonic waves, plasma, flame, UV rays, electron beams, overheated steam or the like is being applied.

In order to complete the reaction between the surface-treating agent and the surfaces of the powder particles in the powder surface-treated by the above mixing dispersion device, the powder is dried at a temperature of 100° C. to 170° C. for 3 hours to 20 hours, for example.

As a particularly preferable embodiment in this explanation, the easy dispersability is further enhanced by pulverizing the surface-treated powder by using the jet mill pulverizer after mixing and contacting the above powder. The jet mill is broadly classified into a flowing layer type, a spiral type, a jet automizer type and the like. Although any type may be used, the flowing layer type which can uniformly and effectively carry out the treatment is most preferable.

A jet stream is ejected through one or plural ejecting holes or ejecting nozzles provided inside the pulverizer. A gas to be used as the jet stream, air, a nitrogen gas, a helium gas, steam and the like are recited, and it may be selected depending upon the powder to be treated and the properties of the surface-treating agent.

The lipophilically surface-treated powder of the present invention exhibiting the easy dispersability can be excellently accomplished by the combined process of the pulverization with the jet mill and the surface treatment with the surface-treating agent composed of the mixture of the alkyl alkoxy silane and one kind of a compound or two or more kinds of compounds selected from the reactive organo polysiloxane and the saturated or unsaturated branched fatty acid having 12 to 22 carbon atoms.

The mixing ratio between the powder to be treated and the surface-treating agent is preferably 1 to 30 parts by weight of the surface-treating agent for 100 parts by weight of the powder. The mixing ratio (parts by weight) between (A) the alkyl alkoxy silane and (B) one kind of a compound or two or more kinds of compounds selected from the reactive organo polysiloxane and the saturated or unsaturated branched and fatty acids having 12 to 22 carbon atoms (including a salt form) is preferably A:B=1.0-29.0 to 29.0-1.0. More preferably, A:B=1.0-19.0 to 19.0-1.0. The mixing ratio among two or more kinds of the treating agents in (B) is not particularly limited. Although it differs depending upon the kind of the powder, the sizes, the specific surface area, the oil absorption amount, etc. of the primary particles, the easy dispersibility tends to decrease if the ratio exceeds these ones.

(4) Cosmetics

No limitation is particularly imposed upon cosmetics into which the lipophilically surface-treated powder according to the present invention is mixed. As the formulations of the cosmetics, for example, conventionally publicly known formulations such as an emulsion form, a creamy form, a solid form, a paste form, a gel form, a powdery form, a multilayer from, a moose form, a spray form, etc. can be selected. Specifically, recitation can be made of, as makeup cosmetics, a makeup base, a powder foundation, a liquid foundation, an oily foundation, a stick foundation, pressed powder, a face powder, a white powder, a lip stick, a lip stick overcoat, a lip gloss, a concealer, a blusher, an eye shadow, an eyebrow, an eyeliner, a mascara, an aqueous nail enamel, an oily nail enamel, an emulsion type nail enamel, an enamel top coat, an enamel base coat and the like; as skincare cosmetics, an emollient cream, a cold cream, a whitening cream, an emulsion, a lotion, a beauty essence, a pack, a carmine lotion, a liquid face wash, a face wash foam, a face wash cream, a face wash powder, a makeup cleanser, a body gloss, UV control cosmetics, a lotion and the like such as a sunscreen, a sunburn cream and the like; as hair cosmetics, a hair gloss, a hair cream, a hair shampoo, a hair rinse, a hair color, a hair brushing agent and the like; as antiperspirant cosmetics, a cream, lotion, a powder, a spray type deodorant product and the like; and as others, an emulsions, a soap, a bath agent, a perfume and the like.

Into the cosmetics in which the lipophilically surface-treated powder of the present invention is mixed can be appropriately blended with a pigment dispersant, an oily agent, a surface active agent, a UV absorber, an antiseptic, an antioxidant, a film former, a moisturizing agent, a thickener, a dye, a pigment, a perfume, etc., which are usually used in the cosmetics and the like, so long as it doe not damage the effects of the present invention. Furthermore, in order to enhance usability and improve the characteristics of the powder, two or more kinds of the lipophilically surface-treated powders obtained by the present invention can be blended into the cosmetics as a mixed or composite powder composition, an oily dispersion and the like. For example, in order to enhance the usability and the like, a lipophilically treated talc and a pigment-grade titanium oxide are mixed or made composite. In order to improve the DV shielding power and the like, the lipophilically treated fine particles of titanium dioxide and the lipophilically treated pigment-grade zinc oxide may be mixed or made composite. No particular limitation is made upon the mixing or composite method at this time. For example, a method in which they are mixed or made composite in a dried or wet manner by using the above mixing dispersion device, a method in which the mixed or composite powder is obtained by the spray drier after the mixing in the wet manner, and the like are recited. At this time, a liquid or solid component usable in the cosmetics may be added as a fixing agent.

In addition, the surface-treated inorganic powders thus obtained can be applied as powders to be used as powders, which are widely used in various fields of not only the cosmetics but also a plastic additive, an ink, a painting material, a toner (magnetic powder), chemical fibers, a wrapping material, an electronic material and the like In the following, the present invention will be explained in detail by taking examples, but the present invention is not limited to these examples.

Example 1

Into a Henschel mixer was added 2 kg of fine particulate titanium dioxide (manufactured by Ishihara Sangyo Kaisha, Ltd.: TTO-S-3), and a preliminarily formulated mixed liquid of surface-treating agents including 300 g of octyl triethoxy silane (manufactured by Dow Corning Toray Industries, Ltd.: Z-6341) and 60 g of a reactive organo silicone (manufactured by Shin-Etsu Chemical Co., Ltd.: X-24-9171) was added thereto and stirred for 30 minutes, while being mixed under stirring. Next, after the resultant was pulverized under the condition of a pulverizing pressure of 4 kg and a classification number of rotations of 10,000 rpm by a jet mill (manufactured by Deutsch Alpine Co., Ltd.: 100AFG type), a lipophilically surface-treated powder was obtained by drying the resultant at 110° C. for 9 hours by a hot air drying machine.

Example 2

A lipophilically surface-treated powder was obtained by the same method as in Example 1 except that the fine particulate titanium oxide was replaced by fine particulate zinc oxide (manufactured by TAYCA Corporation: MZ-500).

Example 3

Into 1500 ml of a mixed liquid deionized water/IPA=50/50 was charged 100 g of fine particulate titanium dioxide (TAYCA Corporation MT-500SA), and 8 g of hexyl triethoxy silane (Shin-Etsu Chemical Co., Ltd.: KBE-3063) and 6 g of isopalmitic acid were added thereto. The resultant was dispersed under circulation for 30 minutes by a sand grinder (DYNO-Mill: 1.4 L zirconia vessel & blade, 0.5 mm$\phi$ zirconia beads at a filling rate of 85%). After the dispersion liquid was dried at 100° C. under a reduced pressure for 7 hours by a vacuum drying machine, a lipophilically surface-treated powder was obtained by pulverizing with a jet mill under the condition of a pulverizing pressure of 5 kg and a classifying number of rotations of 10,000 rpm.

Example 4

Into a Henschel mixer was charged 4 kg of titanium dioxide (manufactured by Ishihara Sangyo Kaisha, Ltd.: CR-50), a preliminarily formulated mixed liquid of surface-treating agents of 600 g of methyl triethoxy silane (manufactured by Shin-Etsu Chemical Co., Ltd.: KBE-13), 120 g of a reactive organo silicone (manufactured by Shin-Etsu Chemical Co., Ltd.: X-24-9171) and 100 cc of IPA was added thereto, while being mixed under stirring. The resultant was stirred for 30 minutes under a reduced pressure. Next, the resultant was pulverized with the jet mill (manufactured by Deutsch Alpine: 100AFG type) under the condition of a pulverizing pressure of 4 kg and a classifying number of rotations of 8,000 rpm, a lipophilically surface-treated powder was obtained by drying at 110° C. for 9 hours with the hot air drying machine. A lipophilically surface-treated powder was obtained by surface-treating each of yellow iron oxide (manufactured by Titan Kogyo, Ltd.: Yellow LL-100P), red iron oxide (manufactured by Titan Kogyo, Ltd.: Red R-516PS) and black iron oxide (manufactured by Titan Kogyo, Ltd.: Black BL-100P) according to the same method.

Example 5

Each lipophilically surface-treated powder was obtained under the same producing condition as in Example 4 except that the jet mill was replaced by an atomizer.

Example 6

Into the henschel mixer was charged 4 kg of talc (manufactured by Asada Milling Co., Ltd.: JA-46R), and a preliminarily formulated mixed liquid of surface-treating agents of 200 g of octyl triethoxy silane (manufactured by Dow Corning Toray Corporation: Z-6341), 40 g of the reactive organo silicone (manufactured by Shin-Etsu Chemical Co., Ltd.: X-24-9171) was added thereto, while being mixed under stirring. After the resultant was stirred for 20 minutes and dried at 120° C. for 8 hours by the hot air drying machine, a lipophilically surface-treated powder was obtained by pulverizing with the jet mill (manufactured by Deutsch Alpine: 100AFG type) under the condition of a pulverizing pressure of 5 kg and a classifying number of rotations of 5,000 rpm. With respect to sericite (manufactured by Sanshin Koko Co., Ltd.: FSE), a lipophilically surface-treated powder was obtained by the same producing method.

Comparative Example 1

A surface-treated powder was obtained by the same producing condition as in Example 1 except that the surface-treating agent was 300 g of octyl triethoxy silane only.

Comparative Example 2

A surface-treated powder was obtained by the same producing condition as in Example 2 except that the surface-treating agent was 300 g of the reactive organo silicone only.

Comparative Example 3

With respect to Example 1, Example 3, Example 4, Example 5 and Example 6 described in JP-A 2002-80748, each of MiBrid-treated powders was obtained by using the materials of the surface-treated powders shown in Examples in the present invention.

(Test/Evaluation Methods)

The surface-treated powders produced in Examples and Comparative Examples were evaluated in the following. Testing methods are shown below. Test evaluation systems were according to two standards of a liquid system and a powder system, and further classified into three: evaluation of a body pigment having primary particle sizes in a geometrically optical range, evaluation of a color pigment having primary particle sizes in a Mie scattering range and evaluation of finely particulate powder having particle sizes in a Rayleigh scattering range according to the primary particle diameter of each of the starting raw materials. In the following, "part" means "part by weight".

(1) Evaluation of the Finely Particulate Powder in the Liquid System

Into a disperser were charged 48 parts of cyclomethicone (manufactured by Shin-Etsu Chemical Co., Ltd.: KF995) and 2 parts of an alkyl-modified polyether silicone (Shin-Etsu Chemical Co., Ltd.: KF-6038), and 10 parts of a surface-treated powder was added under stirring at a number of rotations of 3000 rpm. After the resultant was further stirred in the disperser at the number of rotation of 3000 rpm for 3 minutes, 40 parts of water was added thereto, and an emulsion was prepared by further stirring the resultant in the disperser at the number of rotations of 3000 rpm for 3 minutes. This emulsion was coated onto a TAC transparent film by a bar coater #3. After drying at room temperature for 3 hours, an in-vitro SPF value was measured by an SPF analyzer (manufactured by Optometric, Inc.: SPF-290), and a 560 nm transmittance was measured by a spectral photometer (UV-3150 manufactured by Shimadzu Corporation).

(2) Evaluation of Finely Particulate Powder in a Powder System

In a juicer mixer were mixed and stirred 90 g of talc (manufactured by Asada Milling Co., Ltd.: JA-46R) and 10 g of a surface-treated powder for 10 seconds. Next, after 5 g of squalane was added, an evaluation sample was prepared by further mixing and stirring for 10 seconds. An in-vitro SPF value was measured by the SPF analyzer.

(3) Evaluation of a Coloring Pigment in a Liquid System

Into a disperser were charged 63 parts of cyclomethicone (manufactured by Shin-Etsu Chemical Co., Ltd.: KF995) and 2 parts of an alkyl-modified polyether silicone (manufactured by Shin-Etsu Chemical Co., Ltd.: KF-6038), 20 parts of a surface-treated powder was charged thereinto, while being stirred at a number of rotation of 3000 rpm. After the resultant was further stirred in the disperser at a number of rotation of 3000 rpm for 3 minutes, 15 parts of water was added thereto, and an emulsion was prepared by still stirring the resultant in the disperser at a number of 3000 rpm for 3 minutes. This emulsion was coated onto a paper for testing opacity by the bar coater #3, and after drying at room temperature for 3 hours, color measurements of brightness (L* value) and a chroma (C* value) (Nippon Denshokusha Industries, Co., Ltd.: SZ-Σ90) and luster (Nippon Denshokusha Industries, Co. Ltd.: GC-Σ90) were effected. With respect to titanium dioxide, yellow iron oxide and red iron oxide, the white color are of the opacity test paper was measured, and the black color face was measured with respect to black iron oxide. Measurement values were rounded off to the closest whole numbers.

(4) Evaluation of a Coloring Pigment in a Powder System

Into a juicer mixer were charged 95 g of talc (manufactured by Asada Milling, Co., Ltd.: JA-46R) and 5 g of a surface-treated powder, which were mixed and stirred for 10 seconds to obtain an evaluation sample. In a case of evaluating titanium dioxide, 1 g of non-treated black iron oxide was further added and mixed into the above mixture. Brightness and chroma of each sample were measured.

(5) Evaluation of a Body Pigment in a Liquid System

Into a disperser were charged 63 parts of cyclomethicone (Shin-Etsu Chemical Co., Ltd.: KF995) and 2 parts of an alkyl-modified polyether silicone (Shin-Etsu Chemical Co., Ltd.: KF-6038), and 20 parts of a surface-treated powder was charged thereinto, while being stirred at a number of rotations of 3000 rpm. After the resultant was further stirred in the disperser at a number of rotations of 3000 rpm for 3 minutes, 15 parts of water are added thereinto, which was further stirred in the disperser at a number of rotations of 3000 rpm for 3 minutes, thereby obtaining an emulsion. This emulsion was coated onto a TAC transparent film by a bar coater #3, and a luster value (Nippon Denshokusha Industries, Co. Ltd.: GC-Σ90) was measured after drying at room temperature for 3 hours.

(6) Evaluation of Body Pigment in a Powder System

Into a juicer mixer were charged 3 g of red iron oxide (manufactured by Titan Kogyo, Ltd.: R-516PS) and 97 g of a surface-treated powder, and brightness and chromaticness were measured after mixing and stirring for 10 seconds. Evaluation results were shown in the following.

TABLE 1

Evaluation results of finely particulate powders in liquid system

| | Example 1 | Example 2 | Example 3 | Com. Ex. 4 | Com. Ex. 5 |
|---|---|---|---|---|---|
| SPF value | 15.2 | 8.4 | 19.7 | 4.5 | 2.3 |
| Transmittance (%) | 80.5 | 87.9 | 75.3 | 23.4 | 54.3 |

*Com. Ex. means Comparative Example

As is seen from Table 1, the lipophilically surface-treated powders of the present invention have excellent SPF values and transparency, and the mixing ratio between the powder to be treated and the surface-treating agent are that the surface-treating agent is 1 to 30 parts by weight relative to 100 parts by weight of the powder.

TABLE 2

Evaluation results of finely particulate powders in powder system

|  | Example 1 | Example 2 | Example 3 | Com. Ex. 1 | Com. Ex. 2 |
|---|---|---|---|---|---|
| SPF value | 16.0 | 7.7 | 18.6 | 4.1 | 3.5 |

As is seen from Table 2, the lipophilically surface-treated powders of the present invention have excellent SPF values, and are better in the easy dispersability as compared with the prior art products.

TABLE 3

Evaluation results of color pigments in liquid system

|  | L * value | C * value | Luster value |
|---|---|---|---|
| Titanium dioxide in Example 4 | 68 | 16 | 91 |
| Yellow iron oxide in Example 4 | 39 | 35 | 90 |
| Red iron oxide in Example 4 | 30 | 43 | 94 |
| Black iron oxide in Example 4 | 18 | 8 | 83 |
| Titanium dioxide in Example 5 | 60 | 15 | 87 |
| Yellow iron oxide in Example 5 | 45 | 30 | 85 |
| Red iron oxide in Example 5 | 39 | 38 | 88 |
| Black iron oxide in Example 5 | 25 | 10 | 80 |
| Titanium dioxide in Com. Ex. 3 | 52 | 17 | 71 |
| Yellow iron oxide in Com. Ex. 3 | 45 | 25 | 70 |
| Red iron oxide in Com. Ex. 3 | 39 | 31 | 73 |
| Black iron oxide in Com. Ex. 3 | 29 | 11 | 54 |

As is seen from Table 3, the lipophilically surface-treated pigment-grade powders according to the present invention have excellent coloring power and luster, and are better in ease of dispersion as compared with the prior art products,

TABLE 4

Evaluation results of color pigments in powder system

|  | L * value | C * value |
|---|---|---|
| Titanium dioxide in Example 4 | 76 | 18 |
| Yellow iron oxide in Example 4 | 42 | 30 |
| Red iron oxide in Example 4 | 36 | 38 |
| Black iron oxide in Example 4 | 24 | 11 |
| Titanium dioxide in Example 5 | 70 | 17 |
| Yellow iron oxide in Example 5 | 46 | 27 |
| Red iron oxide in Example 5 | 40 | 33 |
| Black iron oxide in Example 5 | 25 | 10 |
| Titanium dioxide in Com. Ex. 3 | 64 | 15 |
| Yellow iron oxide in Com. Ex. 3 | 48 | 21 |
| Red iron oxide in Com. Ex. 3 | 42 | 28 |
| Black iron oxide in Com. Ex. 3 | 29 | 10 |

As is seen from Table 4, the lipophilic surface-treated pigment-grade powders according to the present invention have excellent coloring power, and are better in the easy dispersability as compared with the prior art products,

TABLE 5

Evaluation results of body pigments in liquid system

|  | Luster value |
|---|---|
| Sericite in Example 6 | 84 |
| Talc in Example 6 | 80 |
| Sericite in Com. Ex. 3 | 66 |

As is seen from Table 5, the lipophilically surface-treated pigment-grade powders according to the present invention have excellent luster, and are better in the ease of dispersibility as compared with the prior art product,

TABLE 6

Evaluation results of body pigments in liquid system

|  | L * value | C * value |
|---|---|---|
| Sericite in Example 6 | 54 | 22 |
| Talc in Example 6 | 52 | 23 |
| Sericite in Com. Ex. 3 | 49 | 16 |

As is seen from Table 6, the lipophilically surface-treated body pigments according to the present invention have excellent coloring strength, and are easier to disperse as compared with the prior art product.

(Producing Examples)

Sample Example 1

Production of Two-Way Powder Foundation

A powder foundation having a composition shown in Table 7 was produced by a below-mentioned method.

TABLE 7

Producing Example 1

| Ingredients | Weight part |
|---|---|
| (1) Sericite (Example 6 and Com. Ex. 3) | to 100.0 |
| (2) Titanium dioxide (Example 4 and Com. Ex. 3) | 8.8 |
| (3) Yellow iron oxide (Example 4 and Com. Ex. 3) | 3.6 |
| (4) Red iron oxide (Example 4 and Com. Ex. 3) | 1.4 |
| (5) Black iron oxide (Example 4 and Com. Ex. 3) | 0.3 |
| (6) Octyl dodecyl oleate | 3.0 |
| (7) Squalene | 4.0 |
| (8) Dimethyl polysiloxane (100cs) | 1.5 |
| (9) Antiseptic | Approp. amount |
| (10) Perfume | Approp. amount |

Approp. amount means "Appropriate amount".

Production Method:

The above ingredients (1) to (5) were mixed in a Henschel mixer. After this was transferred into a high-speed mixer, a composition of ingredients (6) to (10) homogenized by mixing under heating was added thereto, which was homogenized by further mixing. After the resultant was passed through a pulverizer and particle sizes were made uniform by sieving, a 2-way powder foundation was produced in an aluminum dish by compression molding under a surface press pressure of 12 MPa.

The cosmetic into which the lipophilically surface-treated powder was mixed was better in make-up effect, and stability as compared with prior art product.

Sample Example 2

Production of Emulsion-Type Foundation

A W/O liquid foundation having a composition shown in Table 8 was produced by the following method.

TABLE 8

| Producing Example 2 | |
|---|---|
| Ingredients | Weight part |
| (1) Decamethyl cyclopentasiloxane | 25.0 |
| (2) Dextrin Fatty Acid Ester | 0.5 |
| (3) Methylphenyl polysiloxane | 2.3 |
| (4) Squalene | 4.2 |
| (5) Isotridecyl isononanoate | 4.5 |
| (6) Polyether-modified silicone (Shin-Etsu Chemical Co., Ltd.: KF-6017) | 3.0 |
| (7) Red iron oxide (Example 4 and Com. Ex. 3) | 1.3 |
| (8) Yellow iron oxide (Example 4 and Com. Ex. 3) | 2.4 |
| (9) Black iron oxide (Example 4 and Com. Ex. 3) | 0.1 |
| (10) Titanium dioxide (Example 4 and Com. Ex. 3) | 8.0 |
| (11) Sericite (Example 6 and Com. Ex. 3) | 1.0 |
| (12) Ethanol | 5.0 |
| (13) 1,3-butylene glycol | 5.0 |
| (14) Sodium chloride | 2.0 |
| (15) Purified water | to 100.0 |
| (16) Antiseptic | Approp. amount |
| (17) Perfume | Approp. amount |

Production Method:

The above ingredients (7) to (11) were preliminarily mixed and pulverized. The preliminarily pulverized mixture of the ingredients (7) to (11) was added into an oily phase in which ingredients (1) to (6) were dissolved and mixed at 70° C., and the resultant was uniformly dispersed by a homodisperser. An aqueous phase in which ingredients (12) to (16) were homogeneously mixed and dissolved at 70° C. was gradually added into the above oily phase, which was uniformly dispersed by a homomixer, and thereafter a liquid foundation was produced by making uniform emulsified particles with addition of an ingredient (17).

The cosmetic into which the lipophilically surface-treated powder was mixed was better in usability, make-up effects and stability as compared with the prior art product.

Sample Example 3

Production of an Emulsion Type Sunscreen Cream

An emulsion type sunscreen cream having a composition shown in Table 9 was produced by the below-mentioned method.

TABLE 9

| Producing Example 3 | |
|---|---|
| Ingredient | Weight Part |
| 1. Volatile liquid isoparaffin (Isohexadecane) | 15.0 |
| 2. Dimethicone (6cs) | 2.0 |
| 3. Isotridecyl isononanoate | 3.5 |
| 4. Cetanol | 1.0 |
| 5. Squalane | 5.0 |
| 6. Polyethylene glycol monostearate (4EO) | 1.0 |

TABLE 9-continued

| Producing Example 3 | |
|---|---|
| Ingredient | Weight Part |
| 7. Hexaglyceryl polyricinoleate | 3.5 |
| 8. Finely particulate titanium dioxide/isododecane dispersion*1 (Example 1 and Com. Exam. 1) | 10.0 |
| 9. Purified water | Balance |
| 10. Glycerin | 5.0 |
| 11. 1,3-butylene glycol | 5.0 |
| 12. Soda pyrrolidonecarboxylate | 2.5 |
| 13. Antiseptic | Approp. amount |
| 14. Perfume | Approp. amount |

*1 A dispersion was obtained in a bead mill from the addition of 10% of a polyether-modified silicone (Dow Corning Toray Corporation: BY-11-030) into a mixture of a surface-treated powder/isododecane = 4/6, and 10 parts was mixed in an amount of 10 parts as to the surface-treated powder.

(Producing Method)

After an oily component of ingredients (1) to (7) was dissolved at 75° C., an ingredient (8) was added thereto. After an aqueous component of ingredients (9) to (13) was dissolved at 75° C., a homogenized one was added into the oily component, which was emulsified by the homomixer. An ingredient (14) was added thereto, and a sunscreen cream was produced by cooling.

The In-vitro SPF value of the cosmetic into which the lipophilically surface-treated powder was mixed was 23, and that of the prior art product was 17. Further, the cosmetic into which the lipophilically surface-treated powder was mixed had excellent usability, make-up effects and stability.

Sample Example 4

Production of UV Cut Powder Foundation

A powder foundation having a composition shown in Table 10 was produced by the following method.

TABLE 10

| Producing Example 4 | |
|---|---|
| Ingredient | Part by weight |
| (1) Sericite (Example 6 and Com. Ex. 3) | to 100.0 |
| (2) Titanium dioxide (Example 4 and Com. Ex. 3) | 8.5 |
| (3) Yellow iron oxide (Example 4 and Com. Ex. 3) | 3.5 |
| (4) Red iron oxide (Example 4 and Com. Ex. 3) | 1.8 |
| (5) Black iron oxide (Example 4 and Com. Ex. 3) | 0.2 |
| (6) Composite powder of non-treated talc/finely particulate zinc oxide (Example 2 and Com. Ex. 2)*2 | 20.0 |
| (7) Octyldodecyl oleate | 3.0 |
| (8) Squalane | 4.0 |
| (9) Dimethyl polysiloxane | 1.5 |
| (10) Antiseptic | Approp. amount |
| (11) Perfume | Approp. amount |

*2 A non-treated talk JA-46R and each surface-treated finely particulate zinc oxide were charged into the Henschel mixer at a weight ratio of 6/4, and then after mixing and stirring, the mixture was made composite under stirring through dropwise addition of an acryl silicone (Dow Corning Corporation: FA4001CM).

(Production Method)

The above ingredients (1) to (6) were mixed and pulverized by passing them through a pulverizer. The resultant was transferred to a high-speed blender, and a mixture in which ingredients (7) to (11) were heated, mixed and homogenized was added thereinto, which was homogenized by further mixing. After the particle sizes were made uniform by passing the resultant through the pulverizer and sieving it, a UV cut powder foundation was produced in an aluminum dish at a surface press pressure of 10 MPa by compression molding.

The In-vitro SPF value of the cosmetic into which the lipophilically surface-treated powder according to the present invention was mixed was 15, and that of a prior art product was 7. In addition, the cosmetic into which the lipophilically surface-treated powder was mixed was excellent in usability, make-up effects and stability.

What is claimed is:

1. A surface-treated powder, comprising a powder treated with a surface-treating agent composed of a mixture (A+B) between (A) an alkyl alkoxy silane expressed by the following general formula (1) and (B) one compound or two or more compounds selected from a reactive organo silicone expressed by the following general formula (2) and a saturated or unsaturated branched fatty acid having 12 to 22 carbon atoms or a salt form thereof;

$$(C_nH_{2n+1})_aSi(OC_mH_{2m+1})_b \qquad (1)$$

wherein n denotes an integer of 1 to 18, m denotes an integer of 1 to 3, a and b independently denote an integer of 1 to 3, and a+b=4;

$$(R^1{}_3SiO)(R^1{}_2SiO)_p(SiR^2{}_3) \qquad (2)$$

wherein each $R^1$, which are all mutually independent, denotes a lower alkyl group having 1 to 4 carbon atoms or a hydrogen atom, respectively, $R^2$ denotes any of an amino group, a hydrogen atom, a hydroxyl group and a lower alkoxy group having 1 to 4 carbon atoms, and p is an integer of 1 to 300.

2. The surface-treated powder set forth in claim 1, wherein the surface-treating agent is composed of the alkyl alkoxy silane and the reactive organo silicone.

3. The surface-treated powder set forth in claim 1, wherein the surface-treating agent is composed of the alkyl alkoxy silane and the branched fatty acid.

4. The surface-treated powder set forth in claim 1, wherein in the general formula (1), n is 1 to 8.

5. The surface-treated powder set forth in claim 1, wherein in the general formula (2), p is 2 to 50.

6. The surface-treated powder set forth in claim 1, wherein a mixing weight ratio of (A):(B) is 1.0 to 29.0 parts: 29.0 to 1.0 parts.

7. The surface-treated powder set forth in claim 1, wherein a mixing ratio between the powder to be surface-treated and the surface-treating agent is such that the surface-treating agent is 1 to 30 parts by weight per 100 parts by weight of the powder.

8. The surface-treated powder set forth in claim 1, wherein the surface-treated powder is a surface-treated powder further pulverized by a jet mill.

9. A cosmetic comprising at least one surface-treated powder as set forth in claim 1 mixed with at least one different cosmetically acceptable ingredient.

* * * * *